(12) United States Patent
Bossard (10) Patent No.: US 9,539,337 B2
(45) Date of Patent: Jan. 10, 2017

(54) COMPOSITIONS COMPRISING TWO DIFFERENT POPULATIONS OF POLYMER-ACTIVE AGENT CONJUGATES

(75) Inventor: Mary J. Bossard, Madison, AL (US)

(73) Assignee: Nektar Therapeutics, San Francisco, CA (US)

(*) Notice: Subject to any disclaimer, the term of this patent is extended or adjusted under 35 U.S.C. 154(b) by 2920 days.

(21) Appl. No.: 11/009,304

(22) Filed: Dec. 10, 2004

(65) Prior Publication Data

US 2005/0186174 A1    Aug. 25, 2005

Related U.S. Application Data

(60) Provisional application No. 60/528,608, filed on Dec. 10, 2003.

(51) Int. Cl.
*A61K 47/48*    (2006.01)

(52) U.S. Cl.
CPC ... *A61K 47/48176* (2013.01); *A61K 47/48215* (2013.01)

(58) Field of Classification Search
CPC .................. A61K 47/48215; A61K 47/48176
USPC ........................................ 424/78.27; 514/12
See application file for complete search history.

(56) References Cited

U.S. PATENT DOCUMENTS

| 4,179,337 A | 12/1979 | Davis et al. |
| 4,855,285 A | 8/1989 | Stevens |
| 5,891,992 A | 4/1999 | Stevens |
| 6,586,398 B1 | 7/2003 | Kinstler et al. |
| 2004/0213759 A1 | 10/2004 | Zalipsky et al. |

FOREIGN PATENT DOCUMENTS

| EP | 1 333 036 | * 8/2003 |
| WO | 96/17626 | 6/1996 |
| WO | 01/02017 | 1/2001 |
| WO | 03/049760 | 6/2003 |
| WO | 2005/000360 | 1/2005 |
| WO | 2005/062949 | 7/2005 |

OTHER PUBLICATIONS

Bailon, et al., "Polyethylene glycol-conjugated pharmaceutical proteins", PSTT, 1(8):352-356, (1998).
Bedu-Addo, et al., "Effects of Polyethyleneglycol Chain Length and Phospholipid Acyl Chain Composition on the Interaction of Polyethyleneglycol-phospholipid Conjugates with Phospholipid: Implications in Liposomal Drug Delivery", Pharm. Research., 13(5):710-717, (1996).
Bowen, et al., "Relationship between molecular mass and duration of activity of polyethylene glycol conjugated granulocyte colony-stimulating factor mutein", Experimental Hematology, 27:425-432, (1999).

(Continued)

*Primary Examiner* — Blessing M Fubara
(74) *Attorney, Agent, or Firm* — Mark A. Wilson (57) ABSTRACT

Compositions comprising two different populations of polymer-active agent conjugates, wherein the weight average molecular weight of the polymers associated with each population is different, are provided. Also provided are methods preparing such compositions and methods for administering such compositions.

46 Claims, 2 Drawing Sheets

(56) References Cited

OTHER PUBLICATIONS

Harvie, et al., "Use of Poly(ethylene glycol)-Lipid Conjugates to Regulate the Surface Attributes and Transfection Activity of Lipid-DNA Particles", J. of Pharm. Sci., 89(5):652-663, (May 2000).
Roberts, et al., "Chemistry for peptide and protein PEGylation", Advanced Drug Delivery Reviews, 54:459-476, (2002).
Wie, et al., "Suppression of Reaginic Antibodies with Modified Allergens III. Preparation of Tolerogenic Conjugates of Common Allergens with Monomethoxypolyethylene Glycols of Different Molecular Weights by the Mixed Anhydride Method", Int. Archs Allergy Appl. Immun., 64:84-99, (1981).
Yamaoka, et al., "Distribution and Tissue Uptake of Poly(ethylene glycol) with Different Molecular Weights after Intravenous Administration to Mice", J. of Pharm. Sci., 83(4):601-606, (Apr. 1994).
Enzon Pharmaceuticals, Inc.: Macromolecular Engineering Technologies, pp. 1-14, (2004).
Nektar Molecular Engineering: Polyethylene Glycol and Derivatives for Advanced PEGylation, pp. 1-20, (Catalog 2003).
Nektar Advanced PEGylation: Polyethylene Glycol and Derivatives for Advanced PEGylation, pp. 1-24, (Catalog 2004).
NOF Corporation: PEG Derivatives Phospholipid and Drug Delivery Materials for Pharmaceuticals, pp. 1-46, (Catalog 2003—1st).
NOF Corporation: PEG Derivatives Phospholipid and Drug Delivery Materials for Pharmaceuticals, pp. 1-50, (Catalog 2003—2nd).
Polypure: Products; PEG amines; PEG acids and amino acids; PEG thiols and disulfides; Biotins, (Apr. 2004).
Quanta Biodesign: Labeling, Derivatization and Crosslinking Reagents for Biological and Related Materials with dPEG™, pp. 1-38, (Catalog Mar. 12, 2004).
Quanta Biodesign: Labeling, Modification and Crosslinking Reagents incorporating our unique monodispersed dPEG™ Technology, pp. 1-31, (Catalog Nov. 5, 2004).
Shearwater Polymers, Inc.: pp. 2-49, (Catalog 1995).
Shearwater Polymers, Inc.: Polyethylene Glycol Derivatives, pp. 1-53, (Catalog 1997-1998).
Shearwater Polymers, Inc.: Polyethylene Glycol and Derivatives, pp. 1-49, (Catalog 2000).
Shearwater Corporation: Polyethylene Glycol and Derivatives for Biomedical Applications, pp. 1-17, (Catalog 2001).
European Examination Report, corresponding to EP Patent Application No. 04813631.1, dated Jun. 4, 2007.
European Examination Report corresponding to EP Patent Application No. 04813631.1 dated Feb. 4, 2009.
Invitation to Pay Additional Fees corresponding to PCT Application No. PCT/US2004/041328 mailed Nov. 3, 2005.
Notification of Transmittal of the International Search Report and the Written Opinion of the International Searching Authority, or the Declaration corresponding to PCT Application No. PCT/US2004/041328 mailed Feb. 2, 2006.
Notification Concerning Transmittal of International Preliminary Report on Patentability corresponding to PCT Application No. PCT/US2004/041328 mailed Jun. 22, 2006.

* cited by examiner

COMPOSITIONS COMPRISING TWO DIFFERENT POPULATIONS OF POLYMER-ACTIVE AGENT CONJUGATES

CROSS REFERENCE TO RELATED APPLICATION

This application claims the benefit of priority to U.S. Provisional Patent Application Ser. No. 60/528,608, filed Dec. 10, 2003, which is incorporated herein by reference.

FIELD OF THE INVENTION

The present invention relates generally to compositions comprising two populations of polymer-active agent conjugates suited to provide a desired pharmacokinetic profile when administered to a patient. In addition, the invention relates to methods for preparing the compositions, pharmaceutical preparations comprising the compositions, and the like.

BACKGROUND OF THE INVENTION

Scientists and clinicians face a number of challenges in their attempts to develop active agents into forms suited for delivery to a patient. Active agents that are polypeptides, for example, are often delivered via injection rather than orally. In this way, the polypeptide is introduced into the systemic circulation without exposure to the proteolytic environment of the stomach. Injection of polypeptides, however, has several drawbacks. For example, many polypeptides have a relatively short half-life, thereby necessitating repeated injections, which are often inconvenient and painful. Moreover, some polypeptides may elicit one or more immune responses with the consequence that the patient's immune system may be activated to degrade the polypeptide. Thus, delivery of active agents such as polypeptides is often problematic even when these agents are administered by injection.

Some success has been achieved in addressing the problems of delivering active agents via injection. For example, conjugating the active agent to a water-soluble polymer has resulted in polymer-active agent conjugates having reduced immunogenicity and antigenicity. In addition, these polymer-active agent conjugates often have greatly increased half-lives compared to their unconjugated counterparts as a result of decreased clearance through the kidney and/or decreased enzymatic degradation in the systemic circulation. As a result of having a greater half-life, the polymer-active agent conjugate requires less frequent dosing, which in turn reduces the overall number of painful injections and inconvenient visits to a health care professional. Moreover, active agents that were only marginally soluble demonstrate a significant increase in water solubility when conjugated to a water-soluble polymer.

Due to its documented safety as well as its approval by the FDA for both topical and internal use, polyethylene glycol has been conjugated to active agents. When an active agent is conjugated to a polymer of polyethylene glycol or "PEG", the conjugated active agent is conventionally referred to as "PEGylated." The commercial success of PEGylated active agents such as PEGASYS® PEGylated interferon alpha-2a (Hoffmann-La Roche, Nutley, N.J.), PEG-INTRON® PEGylated interferon alpha-2b (Schering Corp., Kenilworth, N.J.), and NEULASTA™ PEG-filgrastim (Amgen Inc., Thousand Oaks, Calif.) demonstrates that administration of a conjugated form of an active agent can have significant advantages over the unconjugated counterpart. Conjugates with small molecules such as distearoylphosphatidylethanolamine (Zalipsky (1993) *Bioconjug. Chem.* 4(4):296-299) and fluorouracil (Ouchi et al. (1992) *Drug Des. Discov.* 9(1):93-105) have also been prepared.

Despite these successes, it is often challenging to provide conjugate-containing pharmaceutical preparations that are both pharmacologically active and have the right balance between a fast onset and sustained action. For example, the PEGASYS® brand PEGylated interferon alpha-2a has only about 7% in vitro activity in comparison with the native form of this interferon. While the resulting PEGylated interferon product makes up for the decrease in activity by having a longer half-life, not all pharmaceutical products will have the flexibility for merely providing sustained activity in vivo; many pharmaceutical products would ideally provide both a relatively rapid onset in addition to sustained activity in vivo. Thus, the present invention seeks to solve these and other needs in the art by providing conjugate-containing compositions whereupon administration of the composition to a patient results in a relatively rapid onset followed by relatively sustained activity.

SUMMARY OF THE INVENTION

Accordingly, the invention provides a composition comprising: a first population of polymer-active agent conjugates, each polymer-active agent conjugate comprised of one or more polymers having a weight average molecular weight; and a second population of polymer-active agent conjugates, each polymer-active agent conjugate comprised of one or more polymers having a weight average molecular weight, wherein the weight average molecular weight of the one or more polymers in the first population is different from the weight-average molecular weight of the one or more polymers in the second population.

The invention also provides such a composition wherein each polymer in the first population has a weight average molecular weight in the range of from about 100 Daltons to less than 120,000 Daltons, and each polymer in the second population has a weight average molecular weight in the range of from greater than 100 Daltons to about 120,000 Daltons, wherein the weight average molecular weight of the one or more polymers in the first population is different from the weight-average molecular weight of the one or more polymers in the second population.

In addition, the invention provides such a composition wherein each polymer in the first population has a weight average molecular weight in the range of from about 100 Daltons to less than 20,000 Daltons, and each polymer in the second population has a weight average molecular weight in the range of from greater than 100 Daltons to about 120,000 Daltons, wherein the weight average molecular weight of the one or more polymers in the first population is different from the weight-average molecular weight of the one or more polymers in the second population.

The invention further provides such a composition wherein each polymer in the first population has a weight average molecular weight in the range of from about 100 Daltons to less than 20,000 Daltons, and each polymer in the second population has a weight average molecular weight in the range of from greater than 20,000 Daltons to about 100,000 Daltons.

The invention additionally provides such a composition wherein the absolute difference between the weight average molecular weight of the polymers in the first population and the second population is from about 500 to about 100,000.

Further, the invention provides such a composition wherein the absolute difference between the weight average molecular weight of the polymers in the first population and the second population is from about 2,000 to about 100,000.

The invention also provides such a composition wherein each polymer in both the first an second populations is a poly(ethylene glycol).

Additionally, the invention provides such a composition further comprising a pharmaceutically acceptable excipient, thereby providing a pharmaceutical preparation.

Also, the invention provides a method for a preparing a composition, wherein the method comprises the steps of: (i) providing a first population of polymer-active agent conjugates; (ii) providing a second population of polymer-active agent conjugates; and (iii) combining the first and second populations of polymer-active agent conjugates, thereby forming a mixture of the first and second populations of polymer-active agent conjugates, wherein the first and second populations are different.

The invention further provides a method for providing an initial onset of activity and a delayed onset of activity, wherein the method comprises the steps of: (i) administering to a patient a first population of active-agent polymer conjugates, each polymer-active agent conjugate comprised of one or more polymers having a weight average molecular weight; and (ii) administering to a patient a second population of active-agent polymer conjugates, each polymer-active agent conjugate comprised of one or more polymers having a weight average molecular weight greater than the weight average molecular weight of the one or more polymers in the first population.

Additional and novel features of the invention will be set forth in the description that follows, and in part, will become apparent to those skilled in the art upon reading the following, or may be learned by practice of the invention.

In one embodiment of the invention, a composition is provided comprised of two populations of polymer-active agent conjugates. In the first population, the conjugates are made from polymers each having a weight average molecular weight that is substantially the same. Similarly, the conjugates in the second population are also made from polymers each having a weight average molecular weight that is substantially the same, but different from the weight average molecular weight of the polymers in the first population.

The conjugates in any given population can comprise singly-attached conjugates (i.e., a single polymer attached to a single active agent, or a "1-mer"), as well as multiply-attached conjugates such as two polymers individually attached to a single active agent (or a "2-mer"), three polymers individually attached to a single active agent (or a "3-mer"), and so on. The present description includes conjugates wherein a single polymer is attached to two active agents. Combinations of singly- and multiply-attached conjugates are contemplated as well. Although any polymer can be used to form a conjugate, it is preferred that the polymer is a poly(ethylene glycol). In addition, the conjugate linkage connecting the polymer to the active agent can either be a stable linkage or a releasable (e.g., hydrolyzable) linkage. Moreover, each conjugate within the composition can have a stable linkage or releasable linkage, or the composition can be comprised of a combination wherein some conjugates in the mixture have stable linkage and other conjugates in the composition have a releasable linkage.

In another embodiment of the invention, a method for a preparing a composition is provided. Although any number of methods are available for preparing the compositions described herein, an exemplary method comprises the steps of: (i) providing a first population of polymer-active agent conjugates; (ii) providing a second population of polymer-active agent conjugates; and (iii) combining the first and second populations of polymer-active agent conjugates, thereby forming a mixture of the first and second populations of polymer-active agent conjugates, wherein the first and second populations are different from each other. No matter which approach is used in preparing the compositions, it is preferred that a mixing step is included following the combining step in order to provide a substantially homogeneous composition. Advantageously, a pharmaceutically acceptable excipient can be added to the composition, thereby resulting in a pharmaceutical composition.

As will be explained in further detail below, one advantage of the presently described compositions is the ability to provide a desired pharmacokinetic profile upon administration to a patient. Thus, a method is provided for providing an initial onset of activity and a delayed onset of activity, wherein the method comprises the steps of: (i) administering to a patient a first population of active-agent polymer conjugates, each polymer-active agent conjugate comprised of one or more polymers having a weight average molecular weight; and (ii) administering to a patient a second population of active-agent polymer conjugates, each polymer-active agent conjugate comprised of one or more polymers having a weight average molecular weight greater than the weight average molecular weight of the one or more polymers in the first population. Typically, although not necessarily, administration takes place simultaneously such as when the first and second populations are present in a single composition, which is administered to a patient.

DETAILED DESCRIPTION OF THE INVENTION

Before describing the present invention in detail, it is to be understood that this invention is not limited to particular polymers, synthetic techniques, active agents, and the like, as such may vary.

It must be noted that, as used in this specification and the claims, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes "—CH$_2$CH$_2$—O(CH$_2$CH$_2$O)$_m$—CH$_2$CH$_2$—" and "—(CH$_2$CH$_2$O)$_m$—," depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— monomeric subunits. With respect to specific forms, the PEG can take any number of a variety of molecular weights, as well as structures or geometries such as "branched," "linear," "forked," "multifunctional," and the like, to be described in greater detail below.

The terms "end-capped" or "terminally capped" are interchangeably used herein to refer to a terminal or endpoint of a polymer having an end-capping moiety. Typically, although not necessarily, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled to of interest can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like.

"Non-naturally occurring" with respect to a polymer or water-soluble polymer segment means a polymer that in its entirety is not found in nature. A non-naturally occurring polymer or water-soluble polymer segment may, however, contain one or more subunits or portions of a subunit that are naturally occurring, so long as the overall polymer structure is not found in nature.

The term "water soluble" as in a "water-soluble polymer segment" and "water-soluble polymer" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

"Molecular mass" in the context of a water-soluble, non-naturally occurring polymer of the invention such as PEG, refers to the weight average molecular weight of a polymer, typically determined by size exclusion chromatography, light scattering techniques, or intrinsic velocity determination in 1,2,4-trichlorobenzene. An approach referred to as MALDI by those of ordinary skill in the art can determine a polymer's true mass. The polymers of the invention are typically polydisperse, possessing low polydispersity values of preferably less than about 1.2, more preferably less than about 1.15, still more preferably less than about 1.10, yet still more preferably less than about 1.05, and most preferably less than about 1.03.

As used herein, the term "carboxylic acid" as in a "carboxylic acid" derivative is a moiety having a functional group [also represented as a "—COOH" or —C(O)OH]. Unless the context clearly dictates otherwise, the term carboxylic acid includes not only the acid form, but corresponding esters and protected forms as well. Reference is made to Greene et al. *Protecting Groups in Organic Synthesis* Third Edition, Wiley, New York, 1999 with respect to suitable protecting groups for carboxylic acids and other functional groups.

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

As used herein, the term "functional group" or any synonym thereof is meant to encompass protected forms thereof.

The term "spacer" or "spacer moiety" is used herein to refer to an atom or a collection of atoms optionally used to link one moiety to another. The spacer moieties of the invention may be hydrolytically stable or may include a physiologically hydrolyzable or enzymatically degradable linkage.

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center or with an electrophile.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, ortho esters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in vivo or in vitro. This includes foods, food supplements, nutrients, nutriceuticals, drugs, proteins, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate—typically present in a pharmaceutical preparation—that is needed to provide a desired level of active agent and/or conjugate in the bloodstream or in a target tissue. The exact amount will depend upon numerous factors, e.g., the particular active agent, the components and physical characteristics of the pharmaceutical preparation, intended patient population, patient considerations, and the like, and can readily be determined by one of ordinary skill in the art, based upon the information provided herein and available in the relevant literature.

"Multifunctional" in the context of a polymer of the invention means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer. A "difunctional" polymer means a polymer having two functional groups contained therein, either the same (i.e., homodifunctional) or different (i.e., heterodifunctional).

"Branched," in reference to the geometry or overall structure of a polymer, refers to a polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

The term "patient" refers to a living organism suffering from or prone to a condition that can be prevented or treated by administration of a conjugate as provided herein, and includes both humans and animals.

"Optional" and "optionally" mean that the subsequently described circumstance may or may not occur, so that the description includes instances where the circumstance occurs and instances where it does not.

Turning to the first embodiment of the invention, a composition is provided comprising two different populations of polymer-active agent conjugates. In contrast to previously described conjugate-containing compositions, the mixed population compositions described herein provide both relatively quick onset of pharmacologic action in addition to a relatively long duration of pharmacologic action when administered to a patient. In particular, by providing a relatively quick onset of pharmacologic action, the presently described compositions improve over previously described conjugate compositions, which have traditionally only provided relatively long duration of pharmacologic action.

Advantageously, the presently described compositions provide a relatively quick onset of action and relatively long activity of action by providing two different populations of polymer-active agent conjugate. Thus, the compositions comprise a first population of polymer-active agent conjugates and a second population of polymer-active agent conjugates. In addition to any other differences, the weight average molecular weight of the polymer associated with the first population is different from the weight average molecular weight in the second population of polymer-active agent conjugates.

Because the weight average molecular weight associated with the polymers in each population is not the same, the weight average molecular weight of the polymer associated with one population will necessarily be lower relative to the weight average molecular weight of the polymer associated with the other population. For the sake of consistency only and for clarity in describing the invention, the active-agent conjugates associated with the relatively lower weight average molecular weight will typically be referred to as the "first population" while the active-agent conjugates associated with the relatively higher weight average molecular weight will typically be referred to as the "second population. It must be remembered, however, that the terms "first" and "second" serve only to identify and distinguish the different populations from each other and that no other meaning or value should be attributed. Consequently, it is perfectly acceptable to refer to the population of polymer-active agent conjugates associated with the relatively low weight average molecular weight as the "second population," and the population with the relatively high weight average molecular weight as the "first population."

While not wishing to be bound by theory, it is believed that the difference in the weight average molecular weight associated with the first and second populations provides the desired combined actions of relatively quick onset and long duration. In particular, it is believed that the population of conjugates having the lower molecular weight polymers provides a relatively quick onset not associated with the population of conjugates having the larger molecular weight polymers. Thus, by providing a mixture of each population, the compositions described herein result (upon administration to a patient) in a pharmacokinetic profile having a relatively fast onset as well as relatively long duration.

Both the first and second populations are comprised of polymer-active agent conjugates. A polymer-active agent conjugate is comprised of at least one polymer and at least one active agent.

With respect to the active agent, any active agent can be used and the invention is not limited in this regard. Suitable agents can be selected from, for example, hypnotics and sedatives, psychic energizers, tranquilizers, respiratory drugs, anticonvulsants, muscle relaxants, antiparkinson agents (e.g., dopamine antagnonists), analgesics, anti-inflammatories, antianxiety drugs (e.g., anxiolytics), appetite suppressants, antimigraine agents, muscle contractants, anti-infectives (e.g., antibiotics, antivirals, antifungals and vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents (including contraceptives), sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, antibodies, diagnostic agents, and contrasting agents.

More particularly, the active agent may fall into one of a number of structural classes, including but not limited to small molecules (preferably insoluble small molecules), peptides, polypeptides, proteins, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

Specific examples of active agents suitable for covalent attachment include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones, human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-571, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, $I^{131}$tositumomab, trastuzumab, tuvirumab, visilizumab, tacrine, memantine, rivastigmine, galantamine, donepezil, levetiracetam, repaglinide, atorvastatin, alefacept, vardenafil, sildenafil, and valacyclovir.

Additional agents suitable for covalent attachment include, but are not limited to, adefovir, alosetron, amifostine, amiodarone, aminocaproic acid, aminohippurate sodium, aminoglutethimide, aminolevulinic acid, aminosalicylic acid, amsacrine, anagrelide, anastrozole, aripiprazole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, dutasteride, epirubicin, estramustine, etoposide, exemestane, ezetimibe, fexofenadine, fludarabine, fludrocortisone, fluorouracil, fluoxymesterone, flutamide, fondaparinux, fulvestrant, gamma-hydroxybutyrate, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, nitisinone, octreotide, oxaliplatin, pamidronate, pentostatin, pilcamycin, porfimer, prednisone, procarbazine, prochlorperazine, ondansetron, palonosetron, oxaliplatin, raltitrexed, sirolimus, streptozocin, tacrolimus, pimecrolimus, tamoxifen, tegaserod, temozolomide, teniposide, testosterone, tetrahydrocannabinol, thalidomide, thioguanine, thiotepa, topotecan, treprostinil, tretinoin, valdecoxib, celecoxib, rofecoxib, valrubicin, vinblastine, vincristine, vindesine, vinorelbine, voriconazole, dolasetron, granisetron; formoterol, fluticasone, leuprolide, midazolam, alprazolam, amphotericin B, podophylotoxins, nucleoside antivirals, aroyl hydrazones, sumatriptan, eletriptan, macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred small molecules for coupling to a polymer as described herein are those having at least one naturally occurring amino group or hydroxyl group. Preferred molecules that include an amino group include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymer as described herein include EPO (erythropoietin), IFN-α, IFN-β, consensus IFN, Factor VIII, Factor IX, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof.

Particularly preferred active agents for the present invention include EPO (erythropoeitin) or any pharmacologically active agent having erythropoeitic agonist activity. Active agents having erythropoeitin activity include those described in for example, U.S. Patent Application Publication No. 2002/0081734, International Publication No. WO 96/40749, and U.S. Pat. Nos. 5,106,954, 6,642,353, 6,048,971, 5,986,047, and 5,888,772. Determination of whether any given active agent will have erythropoietic agonist activity can be accomplished using routine experimentation. For example, as explained in U.S. Patent Application Publication 2002/0081734, determination of erythropoeitic agonist activity can be accomplished by measuring the growth (if any) of EPO-dependent human cell line, TF-1, cultured in RPMI 1640 medium containing 10% fetal calf serum when the proposed active agent is placed in contact with the cells. See Kitamura et al. (1989) *Blood* 73:375-380. Active agents that induce the proliferation of these cells are agents that have erythropoeitic activity. Of course, other methods for determining whether an active agent has erythropoeitic agonist activity can be used as well.

The erythropoietin (or any peptidic active agent having erythropoietic agonist activity) is preferably recombinantly produced, although other methods (particularly for smaller-sized peptides) such as solid phase synthetic techniques as described in, for example, Merrifield (1963) *J. Am. Chem. Soc.* 85:2149, can be used as well. It is particularly preferred that the active agent used in accordance with the present invention is human, recombinant erythropoeitin.

With respect to the polymer, any polymer can be used so long as the polymer is non-antigenic and non-immunogenic. In particular, with respect to relatively large active agents (e.g., proteins), it is preferred that the polymer in the conjugate is water soluble. With respect to relatively small active agents (typically nonpeptidic active agents), the polymer in the conjugate can be either water soluble or not. With regard to the polymer associated with conjugates, however, the polymer is typically non-peptidic. Although preferably a poly(ethylene glycol), a polymer suited for use herein can be, for example, other water-soluble poly(alkylene glycols), copolymers of ethylene glycol and propylene glycol and the like, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384, and copolymers, terpolymers, nonrandom block, and random block polymers of any of the foregoing.

Furthermore, although the polymers used in the conjugates of the first population are preferably the same as type (e.g., linear, branched, forked, and so forth) of the polymers used in the second population, the compositions include instances wherein the polymers of each population are different. For example, a poly(ethylene glycol)-type polymer can be used for each of the first and second populations of conjugates. In addition, a poly(ethylene glycol) polymer-type polymer can be used for one population while a copolymer of ethylene glycol and propylene glycol can be used for the other population in the composition.

Additionally, the polymer is often linear, but can be in other forms (e.g., branched, forked, and the like) as will be described in further detail below. In the context of being present within an overall structure, a water-soluble polymer segment has from 1 to about 300 termini.

In addition to the above-described forms of the polymer, the polymer can also be have one or more weak or degradable linkages in the polymer. For example, poly(ethylene glycol) ("PEG") can be prepared with ester linkages in the polymer that are subject to hydrolysis. As shown below, this hydrolysis results in cleavage of the polymer into fragments of lower molecular weight:

-PEG-CO$_2$-PEG-+H$_2$O→-PEG-CO$_2$H+HO-PEG-

Other hydrolytically degradable linkages, useful as a degradable linkage within the polymer, include carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; ortho ester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

The polymer is typically biocompatible and non-immunogenic. With respect to biocompatibility, a substance is considered biocompatible if the beneficial effects associated with use of the substance alone or with another substance (e.g., an active agent) in connection with living tissues (e.g., administration to a patient) outweighs any deleterious effects as evaluated by a clinician, e.g., a physician. With respect to non-immunogenicity, a substance is considered non-immunogenic if use of the substance alone or with another substance in connection with living tissues does not produce an immune response (e.g., the formation of antibodies) or, if an immune response is produced, that such a response is not deemed clinically significant or important as evaluated by a clinician.

Because of its water-solubility, non-immunogenicity and biocompatibility, poly(ethylene glycol) it is a preferred polymer for use in the each of the polymer-active agent conjugate populations of the compositions described herein. Structurally, poly(ethylene glycol) is a linear polymer terminated at each end with hydroxyl groups:

wherein (m') is a positive integer representing the number of repeating monomers (typically from about 2 to about 4000). Conveniently, poly(ethylene glycol) can be abbreviated as "PEG" and whenever a structure is presented wherein "PEG" appears, it will be assumed that the following structure applies:

wherein (m') is as previously defined.

In addition, the polymer can have one or more termini end-capped with a relatively inert group, such as an alkoxy group. Thus, for example, the linear poly(ethylene glycol) shown above can possess a terminus having a relatively inert methoxy group. The structure of "methoxy-poly(ethylene glycol)" is given below:

where (m') is as previously defined. Other end-capping groups other than alkyl are also possible. Exemplary end-capping moieties include those selected from the group consisting alkyloxy, substituted alkyloxy, alkenyloxy, substituted alkenyloxy, alkynyloxy, substituted alkynyloxy, aryloxy, substituted aryloxy, and hydroxy. Preferred end-capping groups are selected from the group consisting of alkyloxy (e.g., methoxy) and hydroxy.

As previously stated, the compositions of the invention comprise first and second populations of conjugates. The conjugates of any given population can be prepared using any technique known to those of ordinary skill in the art. Typically, however, a polymer is allowed to react with an active agent under conditions suited for conjugation. While the previously described polymers may react with certain active agents, a polymeric reagent comprising the polymer attached to a reactive group is often used. The use of such polymeric reagents provides a facile means for attaching a polymer to an active agent, thereby forming a polymer-active agent conjugate.

Representative polymeric reagents and methods for conjugating these polymeric reagents to an active agent are known in the art and further described in Zalipsky et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995) *Advanced Drug Reviews* 16:157-182. Conveniently, many polymeric reagents are commercially available from Nektar Therapeutics (Huntsville, Ala.). These and other polymeric reagents are described in more detail below.

The reactive group of the polymeric reagent can be any group suited to react with an active agent. Generally, the reactive group comprises an electrophilic or nucleophilic group that allows for covalent attachment of the active agent under covalent coupling conditions. Examples of such reactive groups associated with the polymeric reagent include, but are not limited to those selected from the group consisting of hydroxyl (—OH), ester, orthoester, carbonate, acetal, aldehyde, aldehyde hydrate, ketone, ketone hydrate, thione, thione hydrate, hemiketal, sulfur-substituted hemiketal, ketal, alkenyl, acrylate, methacrylate, acrylamide, sulfone, amine, hydrazide, thiol, thiol hydrate, carboxylic acid, isocyanate, isothiocyanate, maleimide succinimide benzotriazole vinylsulfone, chloroethylsulfone, dithiopyridine, vinylpyridine, iodoacetamide, epoxide, glyoxals, diones, mesylates, tosylates, thiosulfonate, tresylate, silane, and protected or activated forms thereof.

With regard to the active agent, preferred groups providing covalent attachment points for a reactive group of a polymeric reagent include amino (preferably a primary amino group), carboxylic acid, and thiol. When the active agent is a peptide, the N-terminus of the peptide can provide a suitable amino group while the C-terminus of the peptide can provide a suitable carboxy group for reacting with a polymeric reagent. A suitable amino group can also be associated with the amino group of a side chain of any lysine residue(s) in the peptide. The side chain of a histidine residue in a peptide can be useful as an attachment point. Similarly, a thiol group of the side chain of a cysteine-containing peptide can be used. In addition, other groups associated with carbohydrates moieties (as in, for example, glycosylated forms of some peptides) of active agents can also be used in forming conjugates with a polymeric reagent.

Exemplary polymeric reagents are described in further detail below.

Exemplary polymeric reagents include those polymeric reagents wherein the reactive group is an electrophile. Such "electrophilically activated" polymer reagents are reactive to amines (such as in a lysine residue) found on some active agents. Nonlimiting examples of specific polymeric reagents useful for forming covalent linkages with available amines associated with some active agents include mPEG-succinimidyl priopionate (as described in U.S. Pat. No. 5,672,662), mPEG-succinimidyl butanoate (as described in U.S. Pat. No. 5,672,662), mPEG-benzotriazole carbonate (as described in U.S. Pat. No. 5,650,234), mPEG-propionaldehyde (as described in U.S. Pat. No. 5,824,784), mPEG-acetaldehyde (as described in U.S. Pat. No. 5,990,237), all of which are available from Nektar Therapeutics (Huntsville, Ala.).

For reference, examples of each derivative are shown below:

mPEG-succinimidyl propionate mPEG-succinimidyl butanoate mPEG-benzotriazole carbonate mPEG-priopionaldehyde mPEG-acetaldehyde diethyl acetal wherein (n) represents the number of times the ethylene oxide monomer is repeated.

Ketone-, ketone hydrate-, hemiketal-, and ketal-bearing polymeric reagents (as well as their corresponding sulfur-substituted forms) are also useful for conjugation reactions to amines. A particular benefit of these polymeric derivatives is their relative stability (at least as compared to the corresponding aldehyde forms) that allows for more specific and directed conjugation.

Branched versions of electrophilically activated polymers are also known, such as "mPEG2-N-hydroxysuccinimide" and "mPEG2-aldehyde," as shown below:

mPEG2-N-hydroxysuccinimide mPEG2-aldehyde wherein (n) represents the number of times the ethylene oxide monomer is repeated.

Again, reagents such as the "mPEG2-N-hydroxysuccinimide" and "mPEG2-aldehyde" are available from Nektar Therapeutics (Huntsville, Ala.).

Conventional coupling reactions using known reaction conditions can be employed in order to conjugate the polymeric reagent to the active agent. Such reactions and conditions are explained in the relevant literature as well as in many of the articles, patents, and patent publications cited herein.

Typical of one approach is a reductive amination reaction used, for example, to conjugate primary amines with a polymer functionalized with a ketone or aldehyde. In this approach, the primary amine of an active agent reacts with the carbonyl group of the aldehyde or ketone, thereby forming a Schiff base. The Schiff base, in turn, can then be reductively converted in the presence of sodium borohydride to form a stable conjugate. At lower pHs, selective reactions at the N-terminus are possible. In this way, specific conjugates (e.g., conjugates having from one to three water-soluble polymers covalently attached) are possible.

Other polymeric reagents are available that react with groups of an active agent other than amine. For example, if the polymeric reagent is end-functionalized or "activated" with a hydroxyl group, an ester linkage can be formed by reacting the hydroxy-terminated polymeric reagent with a carboxylic acid group-containing active agent. Moreover, if the polymeric reagent is functionalized with a thiol group, a thioester linkage will form between the thiol of the polymeric reagent and the carboxylic acid group-containing active agent.

Additional polymeric reagents include those containing a hydrazide moiety. Such hydrazide-containing polymeric reagents are also useful for conjugation to any available carboxyl group of an active agent. An example of such a polymeric reagent includes a polymeric reagent having the following structure:

where POLY is a polymer.

Polymeric reagents are known that react with thiol groups (such as in a cysteine residue) of an active agent. Nonlimiting examples of specific polymeric reagents useful for forming covalent linkages with available thiol groups associated with some active agents include an N-maleimidyl polymeric reagent as described in U.S. Pat. No. 5,739,208 and in International Patent Publication No. WO 01/62827. Exemplary sulfhydryl-selective PEGs for use in this particular embodiment of the invention include mPEG-forked maleimide [mPEG(MAL)$_2$], mPEG2-forked maleimide [mPEG2(MAL)$_2$], mPEG-maleimide (mPEG-MAL), and mPEG2-maleimide (mPEG2-MAL), all of which are available from Nektar Therapeutics, (Huntsville, Ala.).

The structures of these activated PEGS are as follows:
mPEG-CONHCH[CH$_2$CONH(CH$_2$CH$_2$O)$_2$CH$_2$CH$_2$-MAL]$_2$:
mPEG2-lysine-NH—CH[CH$_2$CONH(CH$_2$CH$_2$O)$_2$CH$_2$CH$_2$-MAL]$_2$;
MPEG-MAL; and
mPEG2-lysine-NH—CH$_2$CH$_2$NHC(O)CH$_2$CH$_2$MAL, respectively, wherein in mPEG is monomethoxy PEG, lysine is the amino acid lysine and MAL stands for maleimide, i.e., Additional polymeric reagents conventionally called "thiol selective" polymers are suitable for reacting with thiol groups and are described International Publication No. WO 04/63250, the disclosure of which is hereby incorporated by reference.

Although the polymeric reagent (and, by extension, the polymer in the resulting polymer-active agent conjugate) used to form the conjugates in both populations can have almost any weight average molecular weight (so long as the polymers associated with each population have a different weight average molecular weight), the weight average molecular weight will typically be in one or more of the following ranges: from about 50 Daltons to about 130,000 Daltons; from about 100 Daltons to about 100,000 Daltons; from about 500 Daltons to about 80,000 Daltons; from about 1,000 Daltons to about 50,000 Daltons; from about 2,000 Daltons to about 25,000 Daltons; and from about 5,000 Daltons to about 20,000 Daltons.

Exemplary weight average molecular weights include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 2,000 Daltons, about 2,500 Daltons, about 3,000 Daltons, about 4,000 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 12,500 Daltons, about 15,000 Daltons, about 20,000 Daltons, about 25,000 Daltons, and 30,000 Daltons, about 40,000 Daltons, about 50,000 Daltons, about 60,000 Daltons, about 70,000 Daltons, about 75,000 Daltons, about 80,000 Daltons, about 85,000 Daltons, about 90,000 Daltons, about 100,000 Daltons, and about 120,000 Daltons.

Although many examples of polymeric reagents have been described, additional polymeric reagents are available for forming polymer-active agent conjugates. Thus, the invention is not limited to polymer-active agent conjugates formed from the presently described polymeric regents. Furthermore, the invention is not limited with respect to any specific weight average molecular weight as a wide range of molecular weights are possible.

In order to form each population of polymer-active agent conjugates, a suitable polymeric reagent is allowed to contact an active agent. Those of ordinary skill in the art know or can determine through routine experimentation whether any given polymeric reagent is suited for forming a conjugate with a specific active agent. For example, active agents having one or more amine groups will react with polymeric reagents bearing an electrophilic group, as discussed above. In addition, one may simply contact a proposed polymeric reagent with the active agent and determine whether conjugation has been effected by running the reaction mixture through a size-exclusion column; the relatively large conjugates—comprised of both polymer and active agent—will be elute before both the nonconjugated polymeric reagent and active agent.

Having selected a polymeric reagent and active agent to form a desired population of conjugates, the polymeric reagent is typically added to the active agent in an equimolar amount (with respect to the desired number of groups suitable for reaction with the reactive group) or at molar excess. For example, the polymeric reagent can be added to the target active agent at a molar ratio of about 1:1 (polymer: active agent), 1.5:1, 2:1, 3:1, 4:1, 5:1, 6:1, 8:1, 10:1, 20:1 or 40:1.

The conjugation reaction is allowed to proceed until substantially no further conjugation occurs, which can generally be determined by monitoring the progress of the reaction over time. Progress of the reaction can be monitored by withdrawing aliquots from the reaction mixture at various time points and analyzing the reaction mixture by SDS-PAGE or MALDI-TOF mass spectrometry, high-performance liquid chromatography (HPLC), or any other suitable analytical method. Once a plateau is reached with respect to the amount of conjugate formed or the amount of unconjugated polymeric reagent remaining, the reaction is assumed to be complete.

Typically, the conjugation reaction takes anywhere from minutes to several hours (e.g., from 5 minutes to 24 hours or more). The resulting population of polymer-active agent conjugates is preferably, but not necessarily, purified so as to separate out excess reagents, unconjugated reactants (e.g., active agent), undesired multi-conjugated species, and free or unreacted polymeric reagent. The resulting population can also be further characterized using analytical methods such as MALDI, capillary electrophoresis, gel electrophoresis, and/or chromatography.

The conditions of the conjugation reaction can be modified in order to provide a desired result. For example, adjusting the pH of the reaction medium often has an influence on reactivity between the polymeric reagent and the active agent such that the number of polymers attaching to the active agent can be adjusted. For example, an aldehyde-bearing polymeric reagent may react with a certain peptide at a pH of 7.5 such that the predominant species is a conjugate having three polymers individually attached to a single active agent. Conjugation of the same aldehyde-bearing polymeric reagent and peptide at a pH of 6.5, however, may predominantly result in a single polymer attached to the peptide. Such selectivity can be determined by one of ordinary skill in the art by conducting any given conjugation reaction under a range of conditions (e.g., a range of pH conditions) and determining which conditions provide a desired result (e.g., the desired number of polymer attached to the desired number of active agents).

With respect to any given population of polymer-active agent conjugates, the conjugates can be purified to obtain/isolate different conjugated species. Alternatively, and more preferably for lower molecular weight (e.g., less than about 20,000 Daltons, more preferably less than about 10,000 Daltons) polymers, the population of polymer-active agent conjugates can be purified to obtain the distribution of polymers per active agent. For example, each population can be purified to obtain an average of anywhere from one to five PEGs per active agent (e.g., protein), typically an average of about one to three PEGs per active agent (e.g., protein). The strategy for purification of the final conjugate reaction mixture will depend upon a number of factors, including, for example, the molecular weight of the polymeric reagent employed, the particular active agent, the desired dosing regimen, and the residual activity and in vivo properties of the individual conjugate(s).

Although it is preferred to have a single polymer attached to a single active agent, other conjugates having one or more polymers attached to one or more active agents are possible. Furthermore, each population within the composition can have differently numbered polymers attached to differently numbered active agents (e.g., a composition comprising a first population having a mixture of singly attached and doubly attached polymers to an active agent, and a second population having substantially only a singly attached polymer to a single active agent). Exemplary conjugates suited for any population in the composition are provided in Table 1.

TABLE 1

Conjugates Having Exemplary Number of Polymers to Number of Active Agents

| Number of Polymers Per Conjugate | Number of Active Agents Per Conjugate |
|---|---|
| 5 | 1 |
| 4 | 1 |
| 3 | 1 |
| 2 | 1 |
| 1 | 1 |
| 5 | 2 |
| 4 | 2 |
| 3 | 2 |
| 2 | 2 |
| 1 | 2 |
| 5 | 3 |
| 4 | 3 |
| 3 | 3 |
| 2 | 3 |
| 1 | 3 |
| 5 | 4 |
| 4 | 4 |
| 3 | 4 |
| 2 | 4 |
| 1 | 4 |
| 5 | 5 |
| 4 | 5 |
| 3 | 5 |
| 2 | 5 |
| 1 | 5 |

If desired, any given population of conjugates having different molecular weights (due to the number of attached polymers) can be isolated using chromatography or other non-resin separation techniques (e.g., diafiltration, membranes, and so forth). That is to say, gel filtration chromatography as well as other techniques can be used to fractionate differently numbered polymer-to-active agent ratios (e.g., 1-mer, 2-mer, 3-mer, and so forth, wherein "1-mer" indicates one polymer to active agent, "2-mer" indicates two polymers to active agent, and so on) on the basis of their differing molecular weights (where the difference corresponds essentially to the average molecular weight of the water-soluble polymer segments). For example, in an exemplary reaction where a 100,000 Dalton protein is randomly conjugated to a PEG alkanoic acid having a molecular weight of about 20,000 Daltons, the resulting reaction mixture will likely contain unmodified protein (MW 100,000 Daltons), mono-PEGylated protein (MW 120,000 Daltons), di-PEGylated protein (MW 140,000 Daltons), and so forth. While this approach can be used to separate PEG and other polymer-active agent conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., ε-amino groups of lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) protein dye-based assays using a standard such as bovine serum albumin (BSA), (iii) iodine testing for PEG content [Sims et al. (1980) *Anal. Biochem,* 107:60-63], and (iv) sodium dodecyl sulfphate polyacrylamide gel electrophoresis (SDS PAGE), followed by staining with barium iodide for PEG and Coomassie or other dye for the peptide. Other separation techniques known to those of ordinary skill in the art can be used as well.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

As previously indicated, the compositions described herein comprise two different populations of polymer-active agent conjugates wherein the difference between the two populations resides with the weight average molecular weight of the polymer. As a result, the compositions of the present invention can be formed by the following method: (a) preparing a first population of conjugates formed by reacting a polymeric reagent having a certain weight average molecular weight; (b) preparing a second population of conjugates formed by reacting a polymer reagent having a weight average molecular weight different from the weight average molecular weight of the polymeric reagent used in step (a); and (c) combining the first and second populations to form a composition.

The compositions of the invention can also be prepared in a "one-pot" synthetic approach. In this approach, conjugates are formed by combining an active agent and two polymeric reagents, each polymeric reagent having a different weight average molecular weight. Typically, in this approach, the reactive group of each polymeric reagent will be exactly the same. In addition, the polymer of each polymeric reagent will typically be the same (e.g., a PEG), but each will have a different weight average molecular weight.

No matter which approach is used in its formation, an optional step of mixing the composition to form a substantially homogeneous mixture can be carried out using conventional techniques. With respect to the approach involving the separate formation of two different populations, it is preferred to include the optional step of mixing the first and second populations of polymer-active agents to form a substantially homogenous mixture.

The specific weight average molecular weight of the polymer associated with each population for a given purpose (i.e., rapid onset or sustained action) will be known to one of ordinary skill in the art or can be determined without undue experimentation. For example, an appropriate polymer size for the first population of polymer-active agent conjugates can be determined by forming a series of conjugates each having relatively small weight average molecular weights (e.g., 500, 750, 1,000, 2,000, 3,000, 4,000, and 5,000), and then determining (through, for example, administration to an animal test subject) which will provide a desired rapid onset of action (e.g., from 12 hours to 2 days). Similarly, series of conjugates each having relatively large weight average molecular weights (e.g., 10,000, 20,000, 30,000, 40,000, 50,000, 100,000, and 120,000), and then determining (through, for example, administration to an animal test subject) which will provide a desired sustained activity (e.g., from 4 days to several weeks). The required combination necessary for providing both rapid onset and sustained action can then be determined by selecting (i) the conjugate population formed from one of the relatively small weight average molecular weight polymers that was found to provide the desired rapid onset, and (ii) the conjugate population formed from one of the relatively large weight average molecular weight polymers that was provide the desired sustained action.

Exemplary weight average molecular weights include the following: each polymer in the first population has a weight average molecular weight in the range of from about 50 Daltons to less than 30,000 Daltons, and each polymer in the second population has a weight average molecular weight in the range of from greater than 5,000 Daltons to less than about 130,000 Daltons (wherein the weight average molecular weight for the polymers associated with each population is different); each polymer in the first population has a weight average molecular weight in the range of from about 100 Daltons to less than 20,000 Daltons, and each polymer in the second population has a weight average molecular weight in the range of from greater than 20,000 Daltons to about 100,000 Daltons; each polymer in the first population has a weight average molecular weight in the range of from about 1,000 Daltons to about 15,000 Daltons, and each polymer in the second population has a weight average molecular weight in the range of from greater than about 25,000 Daltons to about 50,000 Daltons; each polymer in the first population has a weight average molecular weight in the range of from about 2,500 Daltons to about 10,000 Daltons, and each polymer in the second population has a weight average molecular weight in the range of greater than 30,000 Daltons to about 40,000 Daltons; and each polymer in the first population has a weight average molecular weight of about 5,000 Daltons, and each polymer in the second population has a weight average molecular weight in the range of from about 30,000 Daltons to about 40,000 Daltons.

If a small molecule is used as the active agent in both populations, the weight average molecular weights are typically (although not necessarily) smaller. Thus, exemplary ranges of weight average molecular weights for small molecules include the following: each polymer in the first population has a weight average molecular weight in the range of from about 50 Daltons to less than 5,000 Daltons, and each polymer in the second population has a weight average molecular weight in the range of from greater than 100 Daltons to less than about 10,000 Daltons; each polymer in the first population has a weight average molecular weight in the range of from about 100 Daltons to less than 3,000 Daltons, and each polymer in the second population has a weight average molecular weight in the range of from greater than 200 Daltons to less than about 5,000 Daltons;

and each polymer in the first population has a weight average molecular weight in the range of from about 150 Daltons to less than 1,000 Daltons, and each polymer in the second population has a weight average molecular weight in the range of from greater than 500 Daltons to less than about 3,000 Daltons, wherein (for each example) the weight average molecular weight for the polymers associated with each population is different.

In addition, because the weight average molecular weights associated with each of the different populations are different, it is possible to numerically characterize this difference. For example, the absolute difference between a 5,000 Dalton polymer-active agent conjugate and a 30,000 Dalton polymer-active agent conjugate is 25,000 Daltons. Exemplary absolute differences between the weight average molecular weight of the polymers in the first population and the weight average molecular weight of the second population include the following: from about 500 to about 100,000; from about 2,000 to about 100,000; from about 10,000 to about 100,000; from about 20,000 to about 100,000; from about 30,000 to about 100,000; from about 20,000 to about 40,000; and from about 25,000 to about 35,000. It will be recognized that absolute difference is being used so as to negate the effect performing the calculation and obtaining a result having a negative value.

Each population in the composition will also be associated with a molar ratio. Exemplary molar ratios between the first and second populations of polymer-active agent conjugates include the following: from about 1000:1 to about 100:1; from about 100:1 to about 10:1; from about 10:1 to about 1:1; from about 1:1 to about 1:10; from about 1:10 to about 1:100; and from about 1:100 to about 1:1000.

Advantageously, the specific ratio between the first and second population can be adjusted in order to provide the desired pharmacokinetic profile. For example, a composition comprising an initial 1:1 ratio of the first population to second population can be prepared and administered to a test subject, who is then monitored for pharmacologic activity over time. If the clinical indication would be better addressed by providing more of a rapid onset, the population comprising the smaller polymer in the conjugate could be increased. In addition, if the clinical indication would be better addressed by providing more of a sustained action, the population comprising the larger polymer in the conjugate could be increased. In another approach, a series of compositions, each having a unique ratio of each population could be provided and separately administered to a different patient. Each patient can be monitored over time and the best ratio can be determined by selected composition given to the patient who exhibited the best overall pharmacologic response (as exhibited by sufficiently rapid onset and sustained activity). These and other approaches can be used for optimizing the best ratio between the populations for any given application.

With respect to polymer-active agent conjugates intended for subcutaneous delivery and transdermal delivery, the current invention has particular applicability. This is because subcutaneous delivery and transdermal delivery is influenced by, among other things, the size of the therapeutic agent as any agent must travel through several layers of skin to reach the general circulation. As a result, increasing size of a molecule results in a concomitant increase in time for systemic circulation for subcutaneous and transdermal delivery. Thus, the compositions provided herein can provide both relatively quick onset of action by employing a relatively small polymer associated with a first population of conjugates (to provide relatively small conjugates) that can better travel through dermal layers, as well as a longer duration of action by employing a relatively large polymer associated with a second population of conjugates (to provide relatively large conjugates) that requires more time to travel through dermal layers.

The present invention also includes pharmaceutical preparations comprising the composition as provided herein in combination with a pharmaceutical excipient. Thus, the method for making the compositions herein includes the optional step of adding a pharmaceutically acceptable excipient. Generally, the composition itself will be in a solid form (e.g., a precipitate), which can be combined with a suitable pharmaceutical excipient that can be in either solid or liquid form. For example, the compositions (and corresponding pharmaceutical preparations) can be provided in a lyophilized form or in a solution.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, gels, ointments, tablets, powders, and the like. Other modes of administration are also included, such as pulmonary, rectal, transdermal, transmucosal, oral, intrathecal, subcutaneous, intra-arterial, and so forth. Advantageously, the pharmaceutical preparation (as well as the composition) can be provided in a unit dosage form. In addition, the pharmaceutical preparation (as well as the composition) can be used in a vial (e.g., a glass vial or a plastic vial) or in a syringe to provide a prefilled syringe.

As previously described, the pharmaceutical preparation can be injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others. Typically, the preparation is provided in a dry form (e.g., lyophilized form) for storage and is reconstituted with a suitable liquid diluent. Preferred liquid diluents are selected from the group consisting of bacteriostatic water for injection, dextrose 5% in water, phosphate-buffered saline, Ringer's solution, saline solution, sterile water, deionized water, and combinations thereof.

The invention also includes a method for providing an initial onset of activity and a delayed onset of activity, wherein the method comprises the steps of: (i) administering to a patient a first population of active-agent polymer conjugates, each polymer-active agent conjugate comprised of one or more polymers having a weight average molecular weight; and (ii) administering to a patient a second population of active-agent polymer conjugates, each polymer-active agent conjugate comprised of one or more polymers having a weight average molecular weight greater than the weight average molecular weight of the one or more polymers in the first population. Typically, the first and second populations are administered simultaneously. Simultaneous administration is conveniently effected by administering a pharmaceutical preparation as described herein. It is possible, however, to also administer the first and second populations serially, either one after the other, or after a delay to determine, for example, if the patient is responding to the therapy.

In some circumstances, it may be desirable to administer the mixed populations of polymer-active agent conjugates only as an initial dose with subsequent administrations limited to, for example, the second population of active-agent polymer conjugates associated with the higher weight average molecular weight. Thus, for example, a composition of the invention can be used by emergency medical personnel on an urgent basis, while maintenance of the therapeutic levels of the polymer-active agent can be achieved by administering only a single polymer-active agent population on a routine basis.

The invention also provides a method for administering the pharmaceutical preparation as provided herein to a patient suffering from a condition that is responsive to treatment with polymer-active agent conjugates. The method comprises administering, generally via injection, a therapeutically effective amount of the polymer-active agent conjugates (preferably provided as part of a pharmaceutical preparation). The method of administering may be used to treat any condition that can be remedied or prevented by administration of the particular polymer-active agent compositions. Those of ordinary skill in the art appreciate which conditions a specific polymer-active agent conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

When the conjugates include polymers that can be cleaved from the therapeutic agent, an advantage of compositions is the ability for relatively large polymers to be cleared from the body as result of the decrease in size upon cleavage of the polymer from the rest of the conjugate. Optimally, cleavage of each polymer is facilitated through the use of physiologically cleavable and/or enzymatically degradable linkages such as urethane, amide, carbonate or ester-containing linkages. In this way, clearance of the conjugate (via cleavage of individual polymers) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of conjugates with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

It is to be understood that while the invention has been described in conjunction with the preferred specific embodiments thereof, that the foregoing description as well as the experimental that follow are intended to illustrate and not limit the scope of the invention. Other aspects, advantages and modifications within the scope of the invention will be apparent to those skilled in the art to which the invention pertains. All articles, books, patents, patent publications and other publications referenced herein are hereby incorporated by reference in their entireties.

EXPERIMENTAL

The practice of the invention will employ, unless otherwise indicated, conventional techniques of organic synthesis and the like, which are understood by one of ordinary skill in the art and are explained in the literature. In the following examples, efforts have been made to ensure accuracy with respect to numbers used (e.g., amounts, temperatures, and so forth), but some experimental error and deviation should be accounted for. Each of the following prophetic examples provides unexpected benefits over the prior art.

Example 1

A first population of a linear mono-PEG-conjugated rhEPO conjugates is prepared in accordance with Example 8 in EP 1 333 036. The weight average molecular weight of the polymeric portion of the conjugate in this first composition is 5,000 Daltons.

A second population of a linear mono-PEG-conjugated rhEPO conjugate is prepared in accordance with Example 8 in EP 1 133 036 except that the weight average molecular weight of the polymeric portion of the conjugate in this second composition is 30,000 Daltons.

The first and second populations are then combined and mixed well.

Each of the first population, second population and combined mixture is administered to rats following the protocol described in Example 11 of EP 1 333 036. Briefly, each of the first and second populations and combined mixture is diluted to 2.5 μg/mL (assuming a 1:1: ratio of the first population conjugate to the second population conjugate for the combined mixture) with physiological saline containing 0.05% rat serum albumin and 0.05% Tween 20. Each of the first and second populations and combined mixture is administered to a separate group of rats via a single tail injection at 2 mL/kg.

Blood samples from each rat (via withdrawing blood from the tail vein) from each group are obtained on days 1, 2, 4, 5, 7 10, 15, 21, 29 and 35 following administration. Each blood sample is assayed for its reticulocyte count and hemoglobin level. The approximate and expected averages for each group are provided in FIGS. 1 (reticulocyte count) and 2 (hemoglobin level).

Figure 1:
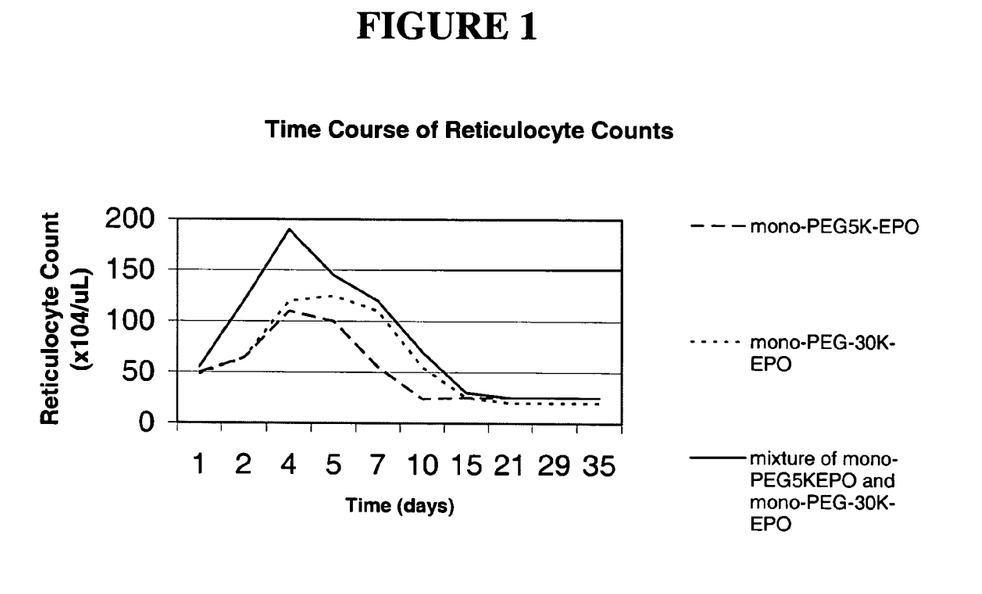
FIGS. 1 and 2 are graphic representations of the approximate and expected results of reticulocyte counts and hemoglobin levels for the conjugates and mixtures described in Example 1 when administered to a patient.
Figure 2:
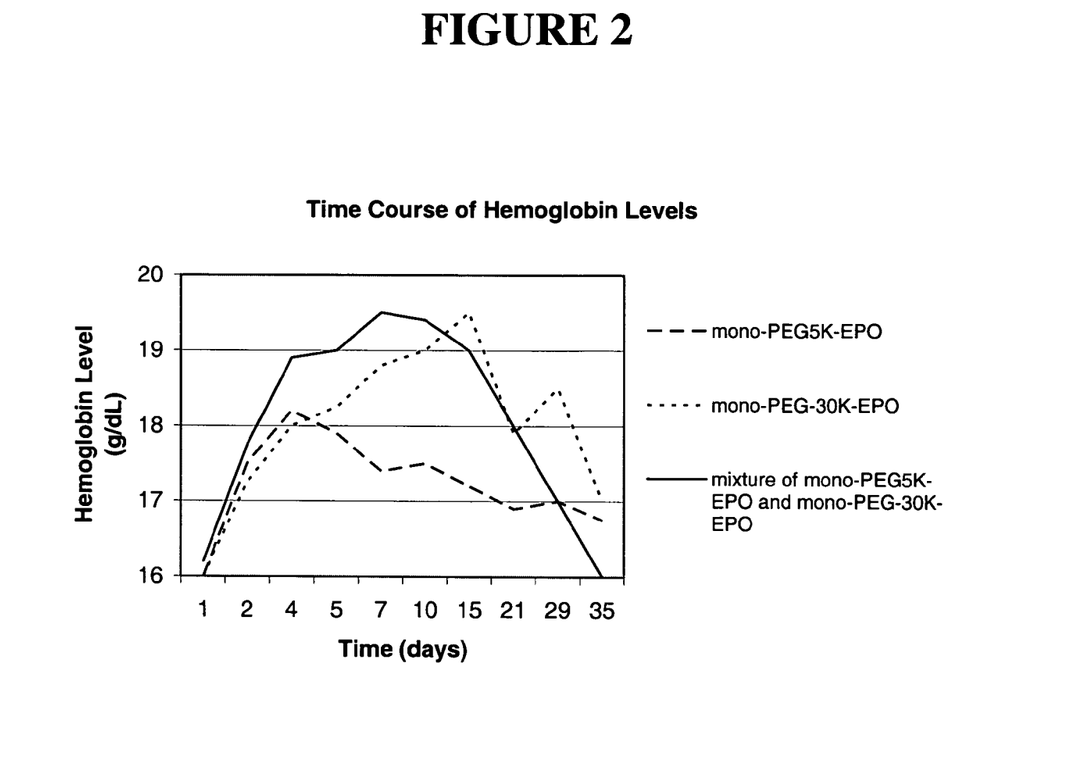

As can be seen from FIGS. 1 and 2, the mixture of combined PEG-EPO conjugates provides a relatively faster onset of action coupled with a relatively sustained action compared to either population administered alone.

Example 2

A first composition comprising a single population of conjugates of interferon (a single polymer attached to a single interferon), wherein the polymer (a PEG) has a relatively small weight average molecular weight (e.g., about 5,000 Daltons), is found to have a relatively quick onset (e.g., about five hours) as evidenced through its $T_{max}$ (i.e., the amount of time following administration for the agent to reach its maximum concentration).

A second composition comprising a single population of conjugates of interferon (a single polymer attached to a single interferon), wherein the polymer (a PEG) has a relatively large weight average molecular weight (e.g., about 40,000 Daltons), is found to have a relatively long onset (e.g., about 96 hours) as evidenced through its $T_{max}$.

Each of the two polymer interferon populations are combined and mixed well to form a single composition comprised of the different populations. Upon administration to a patient subcutaneously, the single composition is expected to provide relatively high levels of a PEG-interferon conjugate quickly (thereby reaching the minimum therapeutic concentration relatively quickly) as well as sustained levels over time (thereby maintaining concentrations above the minimum therapeutic concentration over time).

Example 3

A first composition comprising a single population of conjugates of G-CSF (e.g., filgrastim), wherein the polymer (a PEG) has a relatively small weight average molecular weight (e.g., about 5,000 Daltons), is found to have a relatively quick onset as evidenced through its $T_{max}$ (i.e., the amount of time following administration for the agent to reach its maximum concentration).

A second composition comprising a single population of conjugates of G-CSF (e.g., filgrastim), wherein the polymer (a PEG) has a relatively large weight average molecular weight (e.g., about 20,000 Daltons), is found to have a relatively long onset as evidenced through its $T_{max}$.

Each of the two polymer G-CSF populations are combined and mixed well to form a single composition comprised of the different populations. Upon administration to a patient subcutaneously, the single composition is expected to provide relatively high levels of a PEG-G-CSF conjugate quickly, as well as sustained levels over time, until the post-nadir absolute neutrophil count returns to normal.

Example 4

A first composition comprising a single population of conjugates of insulin, wherein the polymer (a PEG) has a relatively small weight average molecular weight (e.g., about 750 Daltons), is found to have a relatively quick onset as evidenced through its $T_{max}$ (i.e., the amount of time following administration for the agent to reach its maximum concentration).

A second composition comprising a single population of conjugates of insulin, wherein the polymer (a PEG) has a relatively large weight average molecular weight (e.g., about 5,000 Daltons), is found to have a relatively long onset as evidenced through its $T_{max}$.

Each of the two polymer insulin populations are combined and mixed well to form a single composition comprised of the different populations. Upon administration to a patient subcutaneously, the single composition is expected to provide relatively high levels of a PEG-insulin conjugate quickly, as well as sustained levels over time.

What is claimed is:

1. A composition comprising:
   a first population of polymer-active agent conjugates, wherein each polymer in the first population of polymer-active agent conjugates has a weight average molecular weight; and
   a second population of polymer-active agent conjugates, wherein each polymer in the second population of polymer-active agent conjugates has a weight average molecular weight,
   wherein the weight average molecular weight of each polymer in the first population is in the range of from about 100 Daltons to less than 20,000 Daltons, and the weight average molecular weight of each polymer in the second population is in the range of from greater than 100 Daltons to about 120,000 Daltons, wherein the weight average molecular weight of each polymer in the first population is different from the weight average molecular weight of each polymer in the second population.

2. The composition of claim 1, wherein the weight average molecular weight of each polymer in the first population is in the range of from about 100 Daltons to less than 20,000 Daltons, and the weight average molecular weight of each population in the second population is in the range of from greater than 20,000 Daltons to about 100,000 Daltons.

3. The composition of claim 2, wherein the weight average molecular weight of each polymer in the first population is in the range of from about 1,000 Daltons to about 15,000 Daltons, and the weight average molecular weight of each polymer in the second population is in the range of from greater than about 25,000 Daltons to about 50,000 Daltons.

4. The composition of claim 3, wherein the weight average molecular weight of each polymer in the first population is in the range of from about 2,500 Daltons to about 10,000 Daltons, and the weight average molecular weight of each polymer in the second population is in the range of greater than 30,000 Daltons to about 40,000 Daltons.

5. The composition of claim 4, wherein the weight average molecular weight of each polymer in the first population is about 5,000 Daltons, and the weight average molecular weight of each polymer in the second population is in the range of from about 30,000 Daltons to about 40,000 Daltons.

6. The composition of claim 1, wherein the absolute difference between the weight average molecular weight of each polymer in the first population and the weight average molecular weight of each polymer in the second population is from about 500 Daltons to about 100,000 Daltons.

7. The composition of claim 1, wherein the absolute difference between the weight average molecular weight of each polymer in the first population and the weight average molecular weight of each polymer in the second population is from about 2,000 Daltons to about 100,000 Daltons.

8. The composition of claim 1, wherein the absolute difference between the weight average molecular weight of each polymer in the first population and the weight average molecular weight of each polymer in the second population is from about 10,000 Daltons to about 100,000 Daltons.

9. The composition of claim 1, wherein the absolute difference between the weight average molecular weight of each polymer in the first population and the weight average molecular weight of each polymer in the second population is from about 20,000 Daltons to about 100,000 Daltons.

10. The composition of claim 1, wherein the absolute difference between the weight average molecular weight of each polymer in the first population and the weight average molecular weight of each polymer in the second population is from about 30,000 Daltons to about 100,000 Daltons.

11. The composition of claim 1, wherein the absolute difference between the weight average molecular weight of each polymer in the first population and the weight average molecular weight of each polymer in the second population is from about 20,000 Daltons to about 40,000 Daltons.

12. The composition of claim 1, wherein the absolute difference between the weight average molecular weight of each polymer in the first population and the weight average molecular weight of each polymer in the second population is from about 25,000 Daltons to about 35,000 Daltons.

13. The composition of claim 1, wherein the first and second populations of polymer-active agent conjugates has a molar ratio between them of from about 1000:1 to about 100:1.

14. The composition of claim 1, wherein the first and second populations of polymer-active agent conjugates has a molar ratio between them of from about 100:1 to about 10:1.

15. The composition of claim 1, wherein the first and second populations of polymer-active agent conjugates has a molar ratio between them of from about 10:1 to about 1:1.

16. The composition of claim 1, wherein the first and second populations of polymer-active agent conjugates has a molar ratio between them of from about 1:1 to about 1:10.

17. The composition of claim 1, wherein the first and second populations of polymer-active agent conjugates has a molar ratio between them of from about 1:10 to about 1:100.

18. The composition of claim 1, wherein the first and second populations of polymer-active agent conjugates has a molar ratio between them of from about 1:100 to about 1:1000.

19. The composition of claim 1, wherein each polymer in the first and second populations of polymer-active agent conjugates is independently selected from the group consisting of a poly(alkylene oxide), poly(vinyl pyrrolidone), poly(vinyl alcohol), polyoxazoline, poly(acryloylmorpholine), and poly(oxyethylated polyols).

20. The composition of claim 1, wherein each polymer is a poly(ethylene glycol).

21. The composition of claim 20, wherein each poly(ethylene glycol) is terminally capped with an end-capping moiety.

22. The composition of claim 21, wherein each end-capping moiety is independently selected from the group consisting alkyloxy, substituted alkyloxy, alkenyloxy, substituted alkenyloxy, alkynyloxy, substituted alkynyloxy, aryloxy, substituted aryloxy, and hydroxy.

23. The composition of claim 22, wherein the end-capping moiety is hydroxy.

24. The composition of claim 22, wherein each end-capping moiety is alkoxy.

25. The composition of claim 24, wherein each alkoxy is methoxy.

26. The composition of claim 1, wherein each polymer in the first and second populations of polymer-active agent conjugates independently has a structure selected from the group consisting of homopolymer, alternating copolymer, random copolymer, block copolymer, alternating tripolymer, random tripolymer, and block tripolymer.

27. The composition of claim 1, wherein each of the polymer-active agent conjugates in the first population comprises a single polymer attached to a single active agent.

28. The composition of claim 1, wherein each of the polymer-active agent conjugates in the second population comprises a single polymer attached to a single active agent.

29. The composition of claim 28, wherein the poly(ethylene glycol) is linear.

30. The composition of claim 1, wherein each of the polymer-active agent conjugates in both the first and second populations comprises a single polymer attached to a single active agent.

31. The composition of claim 30, wherein the polymer is a poly(ethylene glycol).

32. The composition of claim 1, wherein the active agent has erythropoietic activity.

33. The composition of claim 1, wherein the active agent is erythropoietin.

34. The composition of claim 33, wherein the erythropoietin is recombinantly derived.

35. The composition of claim 1, wherein the active agent is a small molecule.

36. The composition of claim 35, wherein the liquid diluent is selected from the group consisting of bacteriostatic water for injection, dextrose 5% in water, phosphate-buffered saline, Ringer's solution, saline solution, sterile water, deionized water, and combinations thereof.

37. The composition of claim 1, wherein the active agent is a peptide.

38. The composition of claim 1, wherein the active agent is a protein.

39. The composition of claim 1, further comprising a pharmaceutically acceptable excipient.

40. The composition of claim 39, wherein the excipient is a sugar.

41. The composition of claim 39, in lyophilized form.

42. The composition of claim 39, housed in a glass vial.

43. A method for delivering a pharmaceutical preparation comprising the step of administering to a patient a therapeutically effective amount of the composition of claim 39.

44. The composition of claim 1, further comprising a liquid diluent.

45. The composition of claim 1, in unit dosage form.

46. A gel comprising the composition of claim 1.

* * * * *